| United States Patent [19] | [11] | 4,334,969 |
|---|---|---|
| Steglich et al. | [45] | Jun. 15, 1982 |

[54] PHOTOCHEMICAL PROCESS FOR THE SYNTHESIS OF STROBILURIN

[75] Inventors: Wolfgang Steglich, Bonn-Röttgen; Georg Schramm, Hennef-Lichtenberg; Timm Anke; Franz Oberwinkler, both of Tübingen, all of Fed. Rep. of Germany

[73] Assignee: Hoechst Aktiengesellschaft, Frankfurt am Main, Fed. Rep. of Germany

[21] Appl. No.: 279,737

[22] Filed: Jul. 2, 1981

[30] Foreign Application Priority Data

Jul. 4, 1980 [DE] Fed. Rep. of Germany ....... 3025368

[51] Int. Cl.$^3$ ............................................. B01J 19/08
[52] U.S. Cl. ................................................. 204/158 R
[58] Field of Search .................................... 204/158 R

[56] References Cited

U.S. PATENT DOCUMENTS 3,759,978 9/1973 Lincoln et al. ................. 204/158 R
4,299,973 11/1981 Franck-Neumann et al. ..... 204/158 R Primary Examiner—Howard S. Williams
Attorney, Agent, or Firm—Curtis, Morris & Safford

[57] ABSTRACT

Process for stereoselective synthesis of strobilurin in the (E) configuration, starting from cinnamaldehyde and 2-oxobutyric acid.

1 Claim, No Drawings

PHOTOCHEMICAL PROCESS FOR THE SYNTHESIS OF STROBILURIN

The invention provides a process for the preparation of strobilurin by synthesis.

Recently, the antibiotics strobilurin A and B have been isolated from cultures of Strobilurus tenacellus, which have powerful fungicidal properties and act also against pathogenic fungi in man (see T. Anke, F. Oberwinkler, W. Steglich and G. Schramm, J. Antibiot. 30, 806 (1977); G. Schramm, W. Steglich, T. Anke and F. Oberwinkler, Chem. Ber. 111, 2779 (1978). They are 1-arylhexatrienes of 1 structure (strobilurin A) and 2 structure (strobilurin B), which have a β-methoxyacrylate grouping in (E) configuration decisive for the biological effect at the terminal double bond:

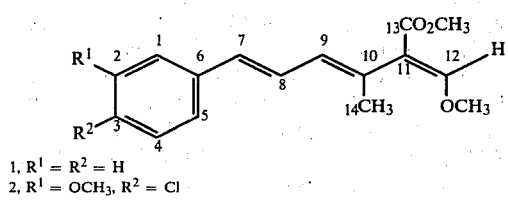

1, $R^1 = R^2 = H$
2, $R^1 = OCH_3$, $R^2 = Cl$

Since only compounds of the cited (E) configuration have a good inhibiting effect, the object of the inventions was to develop a stereoselective synthesis.

In accordance with the invention, a process has been found which allows stereoselective synthesis of strobilurin.

Subject of the invention is therefore a process for the manufacture of synthetic strobilurin in the (E) configuration, which comprises condensing a correspondingly substituted cinnamaldehyde with 2-oxobutyric acid in methanolic KOH to give the correspondingly substituted potassium salt of 3 (Z), 5 (E)-3-methyl-2-oxo-6-phenyl-3,5-hexadienic acid, converting this potassium salt with methanol/thionyl chloride to the corresponding methyl ester, converting the reaction product with methoxymethyl-triphenylphosphorane to 9 (Z) strobilurin, and after chromatographic purification on silica gel irradiating the crude product by means of a mercury vapor lamp in acetone with addition of a small amount of benzene.

The process of the invention is especially suitable for the manufacture of strobilurin A. The reaction proceeds according to the following scheme:

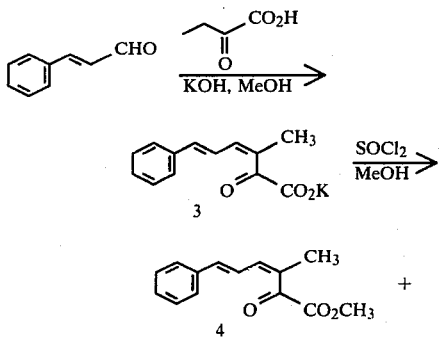

The synthesis of strobilurin A (1) starts from cinnamaldehyde and 2-oxobutyric acid, which are condensed in methanolic KOH to give the potassium salt of 3(Z), 5(E)-3-methyl-2-oxo-6-phenyl-3,5-hexadienic acid (3) (see E. D. Stecher and H. F. Ryder, J. Am. Chem. Soc. 74, 4392 (1952)). The potassium salt is advantageously esterified with SOCl₂/methanol, according to the indications of S. Guttman and R. Biossonas, Helv. Chim. Acta 41, 1852 (1958). The methyl ester 4 is accompanied by about 15 to 18% of the isomeric lactone 5. The mixture can be converted without further purification with methoxymethylene-triphenylphosphorane to the crystalline 9(Z) strobilurin (6) according to the indications of the literature (G. Wittig and E. Knauss, Angew. Chem. 71, 127 (1959); S. G. Levine, J. Am. Chem. Soc. 80, 6150 (1958); G. Wittig, W. Böll and K.-H. Krück, Chem. Ber. 95, 2514 (1962); G. Wittig and M. Schlosser, Chem. Ber. 94, 1373 (1961)). The crude product contains some 9(Z), 11(Z) strobilurin A which, on chromatographic purification on silica gel, is converted to the 6 isomer having an improved thermodynamic stability. Irradiation by means of a mercury vapor lamp (Solidex filter) in acetone with addition of a small amount of benzene brings about a configuration inversion at $\Delta^9$ with formation of strobilurin A (1), which proves to be identical with the natural substance with respect to all spectroscopic properties and its biological effect.

The Wittig reaction with methoxymethylene-triphenylphosphorane has not been applied hitherto to 2-oxocarboxylic acid esters. The complete photochemical isomerization of 6 to the overall trans derivative 1 is surprising.

When using cinnamaldehyde substituted in the aromatic ring as starting material, strobilurin B (2) and analogs are obtained in the manner as described.

Tests:

Potassium salt 3(Z), 5(E)-methyl-2-oxo-6-phenyl-3,5-hexadienic acid (3). 8.4 g of KOH in 25 ml of methanol are added dropwise under N₂ as protecting gas to a mixture cooled to 10° C. and consisting of 10.2 g of 2-oxobutyric acid and 13.2 g of cinnamaldehyde in such a manner that the temperature rises to 25° C. and remains constant on further addition. When adding dropwise the last fourth of the lye, a temperature rise to 45° C. is attained by raising the dropping rate. Immediately after addition is complete the reaction mixture becomes red, and the product precipitates. Agitation is continued for 1 hour at 25° C., and the mixture is abandoned overnight in a refrigerator. Subsequently, the product is suction-filtered and washed 2 to 3 times with a small amount of anhydrous methanol and then 3 to 5 times with anhydrous ether. The potassium salt is then light yellow and in finely powdered state. Yield: 13.5 g (51.2%); m.p. 210°–215° C. (dec.)

3(Z), 5(E)-3-methyl-2-oxo-6-phenyl-3,5-hexadienic acid methyl ester (4)

4.58 g of thionyl chloride are added dropwise at −5° C. to 84 ml of anhydrous methanol. Subsequently, 9.0 g (35 mmols) of potassium salt of 3-methyl-2-oxo-6-phenyl-3,5-hexadienic acid (3) are added, the batch is allowed to take on room temperature, and then refluxed for 20 minutes. After TLC control for complete esterification, KCl is suction-filtered, the filtrate is concentrated, and after-precipitated salt is removed via a G3 frit. Evaporation of the mother liquor and drying in an oil pump vacuum gives 8.0 g of an oil which after several days in a refrigerator solidifies to a wax-like state. According to a $^1$H-NMR spectrum the crude product so obtained contains about 15–18% of 4-methyl-3-methoxy-5-styryl-2,5-dihydrofuran-2-one (5). It can be used for the next reaction step without further purification. Chromatography on silica gel (eluent: methanol) yields the pure ester 4; m.p. 49°–50° C.

$^1$H-NMR([D$_6$]acetone): 2.04 (d, J=1.2 Hz, C-CH$_3$); 3.92 (s, OCH$_3$); 7.18 (d, J=15.6 Hz, 6-H); 7.24 (dq, J=9.4+1.2 Hz, 4-H); 7.4 (dd, covered, 5-H); 7.5 (m, 3H); 7.7 (m, 2H).

9(Z) Strobilurin A (6)

6.5 g (21 mmols) of methoxymethyl-triphenylphosphonium chloride are suspended in 90 ml of absolute ether, and 2.1 g (19 mmols) of potassium tert.-butylate are added under N$_2$. Agitation is continued for 35 minutes at room temperature, and then 3.2 g (14 mmols) of crude 3(Z), 5(E)-3-methyl-2-oxo-6-phenyl-3,5-hexadienic acid methyl ester (4) in 20 ml of ether are added dropwise very rapidly, thus causing the deeply red solution to decolorize nearly completely. After a further 15 minutes' stirring, the mixture is poured into 100 ml of aqueous ammonium chloride solution, extracted, the ether is separated, and the batch is extracted with ether a further 2 times. Evaporation of the organic phases dried over MgSO$_4$ and introduction of the residue dissolved in some ethyl acetate into a silica gel column prepared with petroleum ether (40°–60° C.) (Mallinckrodt) yields (after elution with petroleum ether and subsequently petroleum ether/toluene (1:1) a relatively pure 9(Z) strobilurin A (6) which crystallizes on evaporation. Yield: 1.45 g (40%, relative to the crude ketoester (4); pale yellow crystals, m.p. 75°–77° C.

$^1$H-NMR ([D$_6$]acetone): 1.96 (d, J=1.0 Hz, C-CH$_3$); 3.65 (s, OCH$_3$); 3.88 (s, CO$_2$CH$_3$); 6.15 (dq, J=11.0+1.0 Hz, 9-H); 6.55 (d, J=15.6 Hz, 7-H); 7.22 (dd, J=15.6+11.0 Hz, 8-H); 7.38 (s, 12-H); ~7.4 (m, 5-H).

Strobilurin A' (1)

0.30 g of 9(Z) strobilurin A (6) is irradiated in 6 ml of acetone and 0.6 ml of benzene for 1 hour by means of a mercury vapor lamp with Solidex filter in an irradiation carrousel (Messrs. Dema, Bornheim). Thereafter the isomerization is complete according to TLC (R$_f$ values: 0.47 (4), 0.50 (5); hexane/CCl$_4$/CHCl$_3$/EtOAc=4/3/1/1 on silica gel instant sheets Merck). The product is concentrated by rotation and subjected to chromatography on $^{(R)}$Sephadex LH 20 with methanol. Yield: 0.255 g (85%), colorless oil; identical with natural product. $^1$H-NMR ([D$_6$]acetone): 1.92 (d, J=1.3 Hz, C-CH$_3$); 3.67 (s, OCH$_3$); 3.90 (s, CO$_2$CH$_3$); 6.19 (dq, J=10.0+1.3 Hz, 9-H); 6.48 (d, J=15.6 Hz, 7-H); 6.75 (dd, J=15.6+10.0 Hz, 8-H); 7.48 (s, 12-H); ~7.4 (m, 5-H).

What is claimed is:

1. A process for the manufacture of synthetic strobilurin in the (E) configuration, which comprises condensing a correspondingly substituted cinnamaldehyde with 2-oxo-butyric acid in methanolic KOH to give the correspondingly substituted potassium salt of 3(Z), 5(E)-3-methyl-2-oxo-6-phenyl-3,5-hexadienic acid, converting this potassium salt with methanol/thionyl chloride to the corresponding methyl ester, converting the reaction product with methoxymethylene-triphenylphosphorane to 9(Z) strobilurin, and after chromatographic purification on silica gel irradiating the crude product by means of a mercury vapor lamp in acetone with addition of a small amount of benzene.

* * * * *